US012232931B2

(12) United States Patent
McCarthy et al.

(10) Patent No.: US 12,232,931 B2
(45) Date of Patent: Feb. 25, 2025

(54) EARMUFFS

(71) Applicant: Milwaukee Electric Tool Corporation, Brookfield,, WI (US)

(72) Inventors: Patrick W. McCarthy, Milwaukee, WI (US); Christian R. Braun, Milwaukee, WI (US); Todd Andrew Zeilinger, Wauwatosa, WI (US)

(73) Assignee: Milwaukee Electric Tool Corporation, Brookfield, WI (US)

( * ) Notice: Subject to any disclaimer, the term of this patent is extended or adjusted under 35 U.S.C. 154(b) by 410 days.

(21) Appl. No.: 17/545,748

(22) Filed: Dec. 8, 2021

(65) Prior Publication Data

US 2022/0167701 A1 Jun. 2, 2022

Related U.S. Application Data

(63) Continuation of application No. PCT/US2021/060996, filed on Nov. 29, 2021.

(60) Provisional application No. 63/120,949, filed on Dec. 3, 2020, provisional application No. 63/119,428, filed on Nov. 30, 2020.

(51) Int. Cl.
*A61F 11/14* (2006.01)
*A42B 1/0188* (2021.01)

(52) U.S. Cl.
CPC .............. *A61F 11/14* (2013.01); *A42B 1/0188* (2021.01)

(58) Field of Classification Search
CPC ........ A61F 11/14; A61F 11/12; A42B 1/0188; A42B 3/16; A42B 3/04; A42B 3/30; H04R 1/105; H04R 2201/023; H04R 1/1008; H04R 5/0335
See application file for complete search history.

(56) References Cited

U.S. PATENT DOCUMENTS 2,754,519 A 7/1956 Kindel
3,306,991 A 2/1967 Wood
(Continued)

FOREIGN PATENT DOCUMENTS

CN 2066731 12/1990
CN 1052786 7/1991
(Continued)

OTHER PUBLICATIONS

International Search Report and Written Opinion for International Application No. PCT/US2021/060996, dated Mar. 21, 2022, 10 Pages.

*Primary Examiner* — Ophelia A Hawthorne
(74) *Attorney, Agent, or Firm* — Reinhart Boerner Van Deuren s.c.

(57) ABSTRACT

Earmuffs with a joint are provided to create a biased pressure distribution about a perimeter of the cup. The earmuffs may include a pivot joint. The pressure distribution creates a wedging pressure (e.g., on a top edge) on the cups that hold the earmuffs on the user's head, for example, when the user rotates the headband behind the head. The bias pressure is also used to adjust the seal formed between the pad and the user's head. Adjustments to the moment created by separating the joints from the cup's apex enable a user to selectively adjust the seal according to the user's preference. A cam is added to the headband to change the hoop stress distributed at the joints and further adjust the compressive forces generated to hold the earmuffs against the user's head.

20 Claims, 14 Drawing Sheets

(56) References Cited

U.S. PATENT DOCUMENTS

| | | |
|---|---|---|
| 3,562,816 A | 2/1971 | Hutchinson |
| 3,862,451 A | 1/1975 | Miller et al. |
| 4,027,341 A | 6/1977 | Patteri |
| 4,186,447 A | 2/1980 | Palmaer |
| 4,316,290 A | 2/1982 | Montesi |
| 4,347,631 A | 9/1982 | Newcomb |
| 4,375,702 A | 3/1983 | Lundin |
| 4,471,496 A | 9/1984 | Gardner, Jr. et al. |
| 5,384,857 A | 1/1995 | Nordin et al. |
| 5,546,610 A | 8/1996 | Herzig et al. |
| 6,148,446 A | 11/2000 | Leight |
| 6,611,963 B2 | 9/2003 | Woo et al. |
| 7,766,120 B2 | 8/2010 | Hansson et al. |
| 9,414,965 B2 | 8/2016 | Roos et al. |
| 9,838,776 B2 | 12/2017 | Broadley et al. |
| 9,930,439 B2 | 3/2018 | Nisse et al. |
| 10,350,113 B2 | 7/2019 | Le et al. |
| 10,617,168 B2 | 4/2020 | Winters et al. |
| 10,869,117 B2 | 12/2020 | Prohaszka |
| 10,959,477 B2 | 3/2021 | Nordin et al. |
| 2003/0079275 A1* | 5/2003 | Woo .................. H04R 5/0335 2/209 |
| 2007/0071269 A1 | 3/2007 | Milde |
| 2007/0226865 A1 | 10/2007 | Lindgren |
| 2009/0175481 A1 | 7/2009 | Amae |
| 2013/0219598 A1 | 8/2013 | Pfanner et al. |
| 2017/0264984 A1 | 9/2017 | Princeton |
| 2018/0168270 A1 | 6/2018 | Vaccaro |
| 2019/0320753 A1 | 10/2019 | Le et al. |
| 2020/0154811 A1 | 5/2020 | Hyma |
| 2020/0196698 A1 | 6/2020 | Winters et al. |

FOREIGN PATENT DOCUMENTS

| | | |
|---|---|---|
| CN | 204542565 | 8/2015 |
| CN | 205391247 | 7/2016 |
| CN | 206761828 | 12/2017 |
| CN | 209951558 | 1/2020 |
| CN | 110801073 | 2/2020 |
| DE | 1912241 | 3/1965 |
| DE | 2260311 | 6/1973 |
| DE | 7415619 | 8/1974 |
| DE | 2521033 | 11/1976 |
| DE | 2719503 | 11/1978 |
| WO | WO2020/007606 | 1/2020 |
| WO | WO2021/097056 | 5/2021 |

* cited by examiner

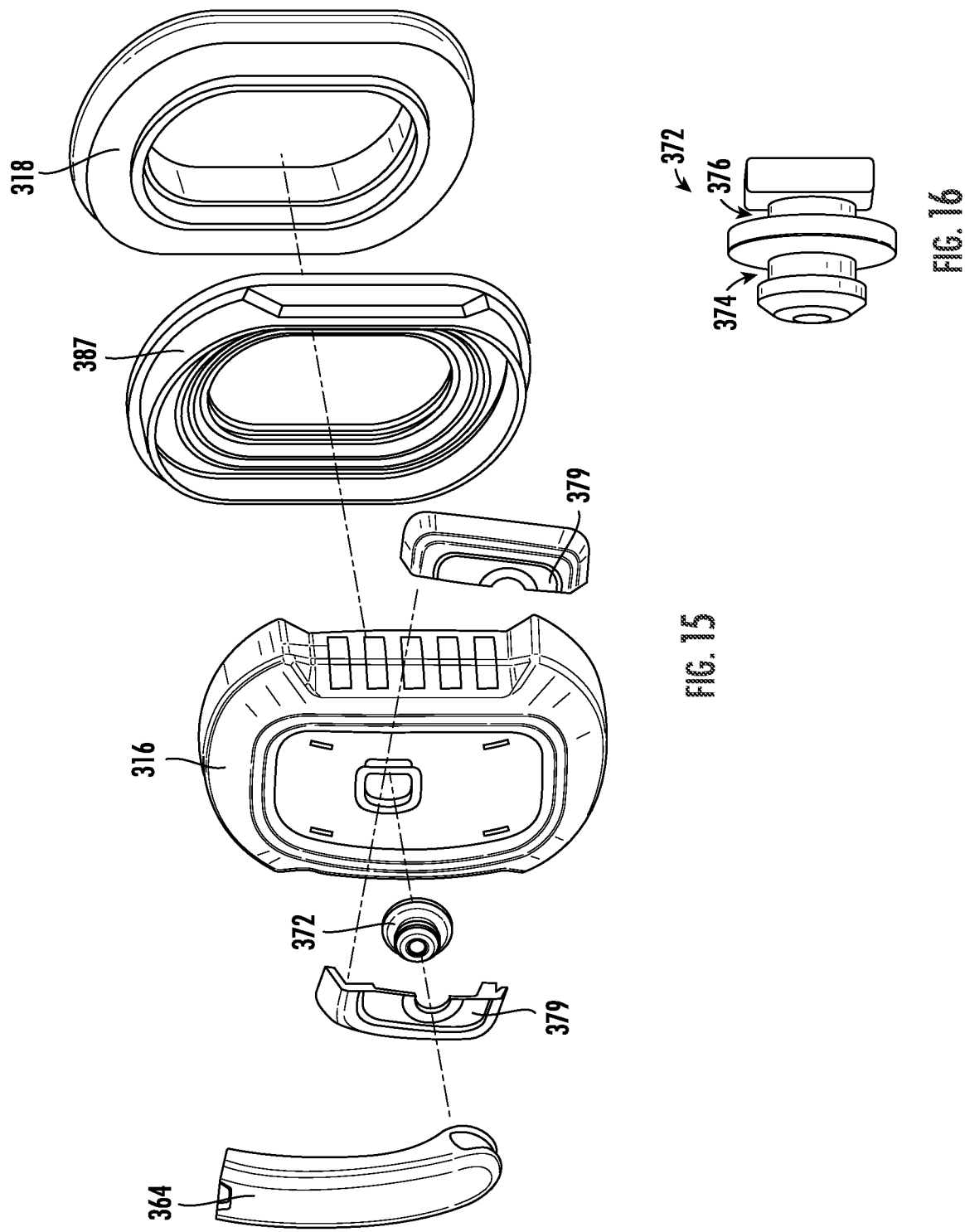

EARMUFFS

CROSS-REFERENCE TO RELATED APPLICATIONS

This application is a continuation of International Application No. PCT/US2021/060996, filed Nov. 29, 2021, which claims the benefit of and priority to U.S. Provisional Application No. 63/119,428, filed Nov. 30, 2020, and U.S. Provisional Application No. 63/120,949, filed Dec. 3, 2020, which are incorporated herein by reference in their entireties.

BACKGROUND OF THE INVENTION

The present invention relates generally to the field of safety equipment. The present invention relates specifically to ear protection. Earmuffs protect a user's ears from the harmful effects of noise, particularly in loud work (e.g., construction) or recreational environments (e.g., firearms).

SUMMARY OF THE INVENTION

One embodiment of the invention relates to earmuffs, including a left ear cup configured to cover the left ear and a right ear cup configured to cover the right ear. The left and right cups each have an outer shell that extends from a top edge to a bottom edge. The edges define a horizontal midplane located between the top edge and the bottom edge. A headband includes a first end coupled to the left cup and a second end coupled to the right cup. A first pivot joint couples the first end of the headband to the left cup, and a second pivot joint couples the second end of the headband to the right cup. The headband includes a left joint located between the horizontal midplane and the top edge of the left cup and a right joint located between the horizontal midplane and the top edge of the right cup. The left joint compressively biases the top edge of the left cup. Similarly, the right joint compressively biases the top edge of the right cup. The compressive bias creates a compressive pressure above the ears that restrains and holds the earmuffs tightly against the user's head when the headband is rotated behind the head.

Various embodiments of the invention relate to earmuffs with joints that, in some instances, coincide with pivot locations. In some instances, pivot locations also directly couple the headband to each cup. In various embodiments, the joint creates a pivot location for the headband located between the horizontal midplane and the top edge of the left and the right outer shells. In another embodiment, the headband has a fixed angle (e.g., a bent "L-band"). The fixed angle headband includes a pivot joint at the end of the headband and an off-center joint that rotates about the pivot joint. The joint rotates around the pivot joint by an offset (e.g., along the lower line segment of the "L") when the headband rotates.

In one embodiment, the headband has a locking pivot at the joint (e.g., the joints coincide with pivot locations, and each includes a selectively lockable pivot). In this configuration, a portion of the headband rotates about each locking pivot from a first position over the user's head to a second position behind the user's head. In various embodiments, the earmuffs include a cam that rotates on the outer shell of the earmuffs (e.g., behind the headband). The cam enables a user to adjust the biased compressive force and customize the force based on the work environment, personal preference, and/or the headband position (e.g., above or behind the head).

In another specific embodiment, a pair of earmuffs includes a first ear cup, a second ear cup, and a band. The band has an upper segment that extends between a first lower band segment and a second lower band segment. A first angle between 45 degrees and 135 degrees is formed between the upper band segment and the first lower band segment, and a second angle between 45 degrees and 135 degrees is formed between the upper band segment and the second lower band segment. The first lower band segment is coupled to the first ear cup by a first pivot joint and the second lower band segment is coupled to the second ear cup by a second pivot joint. When the first ear cup is positioned over a first ear of the user and the second ear cup is positioned over a second ear of the user, the band is configured to rotate about the first pivot joint and the second pivot joint from a first position in which the upper band segment is positioned above a user's head to a second position in which the upper band segment is positioned behind a user's head.

In another specific embodiment, another pair of earmuffs includes a first ear cup, a second ear cup, and a band. The band has a first lower band segment that is coupled to the first ear cup, and a second lower band segment that is coupled to the second ear cup. An upper band segment couples the first lower band segment to the second lower band segment. The upper band segment is coupled to the first lower band segment by a first band pivot joint, and the upper band segment is coupled to the second lower band segment by a second band pivot joint. When the first ear cup is positioned over a first ear of the user and the second ear cup is positioned over a second ear of the user, the upper band segment is configured to rotate about the first band pivot joint and the second band pivot joint, respectively, from a first position in which the upper band segment is positioned above a user's head to a second position in which the upper band segment is positioned behind the user's head.

In another specific embodiment, an earmuff cup assembly includes an ear cup having an outer shell. The outer shell has a first side and a second side opposite the first side. An ear pad is coupled to the first side of the outer shell. The earmuff cup assembly also includes a pivot mount that is coupled to the second side of the outer shell. At least a portion of the pivot mount protrudes from the outer shell. The pivot mount has an exterior annular channel that is formed in the portion of the pivot mount that protrudes from the outer shell. The earmuff cup assembly additionally includes a first band segment with a first end and a second end opposite the first end. The first end pivotably mates with the exterior annular channel. Specifically, a surface of the first band segment forms an opening near the first end that is sized to mate the first band segment with the annular channel of the pivot mount. The first band segment is configured to rotate about the pivot mount and to tilt within the annular channel, such that the second end may be adjusted toward or away from the ear cup.

Alternative exemplary embodiments relate to other features and combinations of features as may be generally recited.

BRIEF DESCRIPTION OF THE DRAWINGS

This application will become more fully understood from the following detailed description, taken in conjunction with the accompanying figures, wherein like reference numerals refer to like elements in which:

FIG. 15 is an exploded view of an earmuff ear cup and headband segment, according to another exemplary embodiment.

FIG. 16 is a perspective view of the pivot joint shown in FIG. 10.

DETAILED DESCRIPTION

Figure 1:
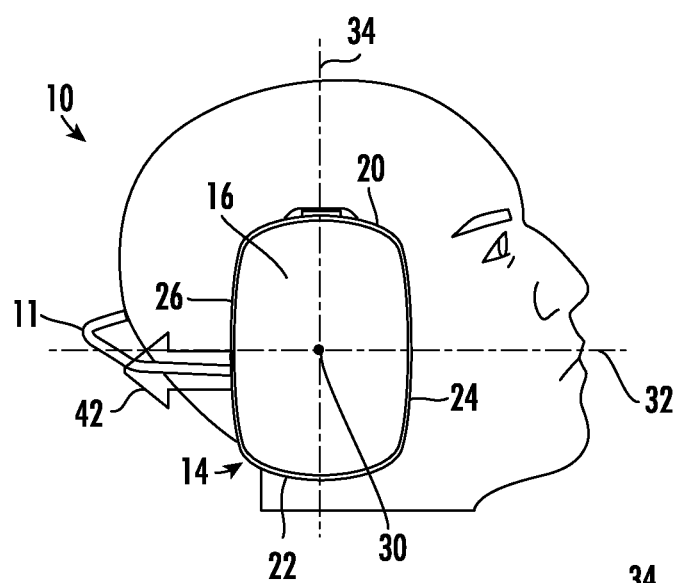
FIG. 1 is an exterior side view of a pair of rear-biased earmuffs with an offset headband, according to an exemplary embodiment.

Referring generally to the figures, various embodiments of earmuffs are shown. Earmuffs are used to protect a user's ears from excessive and/or loud noises. Earmuffs include a headband coupled to a pair of cups (e.g., left and right cups). In various embodiments discussed herein, Applicant has found that providing a headband with a biased or off-center compressive force on the ear cup provides various advantages discussed herein. In particular, Applicant has found that offsetting the pivot location that couples the headband to the earmuffs, from the apex of the ear cup, creates a moment that decouples into a biased force on the seal created between the cup and the user's head. To enhance noise reduction, earmuffs form a seal against the user's head around each ear. In addition, the headband's rotation or movement changes the seal and the pressure created against the user's head. Applicant has found that by moving the pivot connections of the headband on the cups to an off-center location of the cup and/or including separate fixed and/or pivot joints on the headband, the induced moment or biased forces on the cup provides an enhanced seal. Applicant has found that when the headband rotates behind the head, an upwardly compressive bias force (e.g., a moment that creates a compressive force on a top side that is greater than a compressive force on the bottom side of the ear cup) enhances the seal on the cup surrounding the user's ears. The upwardly compressive bias force holds the earmuffs on the user's head, e.g., when the headband is rotated behind the user's head.

Further, in addition to fortifying the seal of the ear cup around a user's ear, it is also important for a pair of earmuffs to remain secured to a user when not covering the ear, for instance when a user needs to communicate with another individual or receive instructions in between periods of loud noise, when external sound levels are reduced. Applicant has found that the moment and related compressive bias force discussed above also serves to improve the securement of the ear cup against the user's head. Further, Applicant has found coupling a headband to an ear cup through use of a pivot joint to increase the quality and comfort of the ear cup against the back portion of a user's head (e.g., behind the user's ear) or against the exterior of a hard hat.

In various embodiments, a compressive force is created through coincident pivot locations and/or joints that are located on the headband and/or cups and that bias the cups against a portion of the user's head. A moment is created by orienting a pivot connection and/or headband joint at an off-center location relative to the apex of the cup. This moment generates a bias force that bias's the ear cup against a particular portion of the user's head. In embodiments that include a headband joint, the location at which the headband connects to the ear cup is offset from the headband joint.

In one embodiment, the headband joint is rigid or fixed, and only one pivot location exists for each cup (specifically, where the headband connects to the ear cup). In another embodiment, the headband joint is a pivot joint that a user adjusts to modify the joint. As used herein, a pivot joint is a location where at least a portion of the headband rotates about a pivot, for example, at the end of the headband (e.g., where the headband connects to the cup, such that the headband pivots or rotates with respect to the cup) or at an offset headband location (e.g., along the headband, such that two portions of the headband pivot with respect to one another).

A joint on the headband distributes the hoop stresses in the headband to create a compressive force on the cup (e.g., a moment force that decouples into different compressive forces on the outer shell and acts towards the user's head). In certain embodiments, the headband includes a rigid joint, formed by two portions of the headband that do not substantially pivot with respect to one another. In some embodiments, the headband joint is a rigid joint and the headband is coupled to the ear cup by a pivot joint. In other embodiments, the headband joint is a pivot joint, and the headband is fixedly connected to the ear cup, such that the headband does not substantially pivot with respect to the ear cup. In various other embodiments, the headband joint is a pivot joint, and the headband is coupled to the ear cup by a pivot joint. In various other embodiments, the headband does not include any joints and is coupled to an off-center location of the ear cup by a pivot joint.

Figure 2:
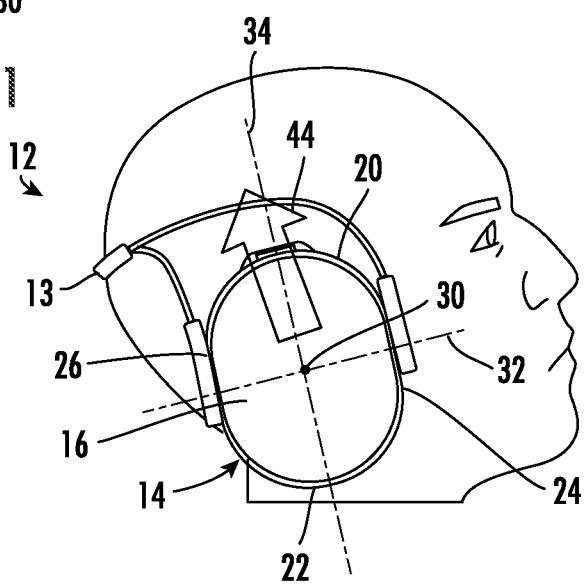
FIG. 2 is an exterior side view of a pair of top biased earmuffs with a headband over the cup, according to an exemplary embodiment.

FIG. 1 shows rear-biased earmuffs 10 coupled to a rear-mounted headband 11. Specifically, headband 11 is coupled to a location at the rear of an earmuff cup or ear cup 14 and extends away from the rear of the ear cup 14 in a generally rearward direction to wrap around a lower portion of the back of the user's head. FIG. 2 shows top biased earmuffs 12 coupled to a top-mounted headband 13. Specifically, headband 13 couples to both an upper front and an upper back location of the ear cup 14 and extends away from the ear cup in a generally upward direction to wrap around an upper section of the back of the user's head. Earmuffs 10 are substantially the same as earmuffs 12, except for the differences discussed herein.

With reference to FIG. 1, rear-biased headband 11 of FIG. 1 couples to an ear cup 14 at a rearward off-center location on an outer shell 16 to create a rearward moment. The rearward moment imparts a greater compressive force on the rear side of cup 14 than on the front side of cup 14. As shown in FIG. 2, top-mounted headband 13 couples to an upper off-center location on cup 14 to create a moment that creates a greater compressive force on the top side of cup 14 than on the bottom side of cup 14. Specifically, headbands 11 and 13 couple to off-center locations (e.g., rearward or upward locations) to create respective moments that produce different forces on different sides of respective cup 14. As shown in FIGS. 1 and 2, the off-center location that couples headband 11 (or 13) to cup 14 generates a moment on cup 14. The distribution of the moment generates different compressive forces on opposite sides of the cup 14. In this way, headband 11 (or 13) creates a compressive force that biases the sides of cup 14 in the direction indicated by the arrow 42 (or 44) to squeeze against the user's head and create a seal.

Cup 14 includes outer shell 16, defining an exterior surface. Cup 14 covers the user's ear, and the compressive forces enhance the seal between cup 14 and the user's head. When the compressive forces on the seal are not equal, a bias exists that pulls the earmuffs 10 in the biased direction. Stated differently, the wedging of cups 14 creates a pulling direction or bias. For example, Applicant has found that changing the location at which headband 13 couples to cup 14, to a location offset from the apex of the cup 14, creates an unequal distribution of forces (e.g., a bias) on cup 14. The biased moment or forces create a compressive pressure on an ear pad, such as pad 418 (shown best in FIGS. 8A-8C) that secures or holds cup 14. The off-center location where headband 13 is coupled to cup 14 creates pressure above the user's ears to hold the earmuffs 12 when headband 13 is rotated or positioned behind the user's head.

Outer shell 16 defines an exterior surface extending vertically from a top edge 20 to a bottom edge 22 and horizontally from a forward or front edge 24 to a rear edge 26. Collectively, the top edge 20, bottom edge 22, front edge 24, and rear edge 26 form a perimeter of cup 14 and/or outer shell 16. The pad extends around the perimeter to create a soft cushion surface that distributes the compressive forces on the perimeter. For example, the compressive force on top edge 20 is made greater than the compressive force on bottom edge 22 to hold earmuffs 10 on the user's head when headband 11 is rotated and/or positioned behind the head.

In some embodiments, outer shell 16 defines a curved or rounded exterior surface with a centrally located local maximum, center point, or apex 30 on cup 14. A horizontal midplane 32 is defined halfway between top edge 20 and bottom edge 22. When edges are curved, tangent lines at top edge 20 and/or bottom edge 22 define horizontal midplane 32. Similarly, a vertical midplane 34 is defined halfway between front edge 24 and rear edge 26. In FIG. 1, headband 11 couples to cup 14 towards the rear side of cup 14. Stated differently, headband 11 couples to cup 14 at a location offset from the vertical midplane 34 in the direction of rear edge 26. This off-center joint creates a compressive force on rear edge 26 that is greater (e.g., different) than the compressive force on front edge 24 and wedges earmuffs 10 towards the back of the head.

Similarly, FIG. 2 shows headband 13 coupled to cup 14 between horizontal midplane 32 and top edge 20. This off-center joint creates a compressive force on top edge 20 that distributes on the pad and securely holds earmuffs 10 to maintain a seal on the user's head, for example, when headband 13 is rotated and/or worn behind the head. Applicant has found that compressive forces (e.g., forces with a vector directed from cup 14 towards the user's head) ensure a secure fit that enhances the seal created against the head. The geometry and/or off-center joint of headband 13 creates the bias force from the decoupled moment. For example, an off-center joint 40 located away from apex 30 creates the bias force to hold the seal when headband 13 is rotated and/or positioned behind the head. In other words, the upward wedging of cups 14 supports the weight of headband 13 when worn behind the user's head.

FIG. 1 shows a rear offset that creates a bias compressive force in the rearward direction, as indicated by arrow 42 (e.g., the compressive force on rear edge 26 is greater than the compressive force on front edge 24). In FIG. 2, the compressive force along top edge 20 is greater than the compressive force along bottom edge 22 to create an upwardly biased compressive force, as indicated by arrow 44. In other words, headband 13 is located behind the head to create a rearward biased compressive force and above cup 14 to create an upwardly biased compressive force. As used herein, an upwardly biased compressive force means that the force on top edge 20 is different (e.g., greater) than the compressive force on bottom edge 22 to create an upward bias on cups 14. Movement or rotational adjustment of headband 11 also changes the bias forces and/or pressure distributions on the pad. Applicant has found that using the geometry and/or location of headband 13 makes earmuffs 12 selectively adjustable to modify the bias forces and/or pressure distributions.

Figure 3:
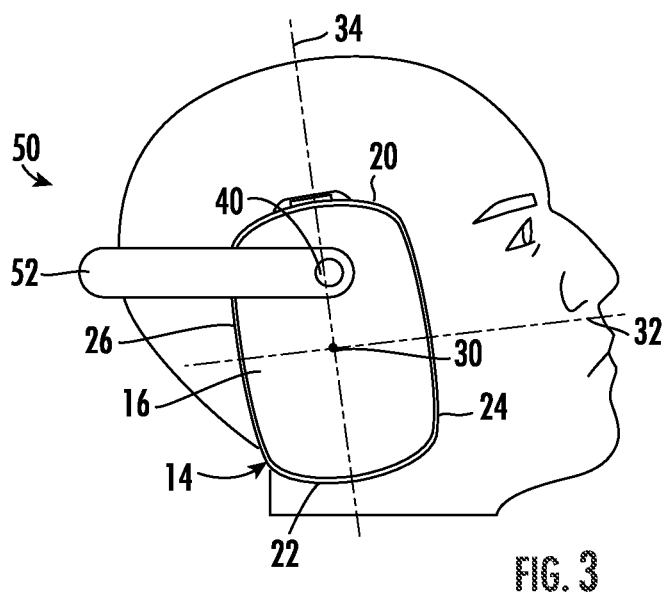
FIG. 3 is an exterior side view of a pair of earmuffs with a straight headband having an off-center pivot joint, according to an exemplary embodiment.

FIG. 3 shows earmuffs 50, according to an exemplary embodiment. Earmuffs 50 are substantially the same as earmuffs 10 and/or 12, except for the differences discussed herein. Earmuffs 50 include a straight headband 52 and an off-center pivot joint 40 that couples headband 52 to ear cup 14. The moment that results from this configuration is distributed as a bias force that acts on outer shell 16. Pivot joint 40 is located between horizontal midplane 32 and top edge 20. In various examples, pivot joint 40 is off-center and/or located above horizontal midplane 32. For example, pivot joint 40 is halfway between top edge 20 and horizontal midplane 32, such that a distance between pivot joint 40 and top edge 20 is equal to a distance between pivot joint 40 and horizontal midplane 32. In various embodiments, pivot joint 40 is located nearer to top edge 20 (e.g., shorter distance) than to horizontal midplane 32 (e.g., longer distance). This configuration increases the moment, which increases the compressive bias force and/or pressure on top edge 20. In other various embodiments, pivot joint 40 is nearer to the horizontal midplane 32 (e.g., shorter distance) than to the top edge 20 (e.g., longer distance) to reduce the compressive bias force and/or moment on cup 14.

Figure 4:
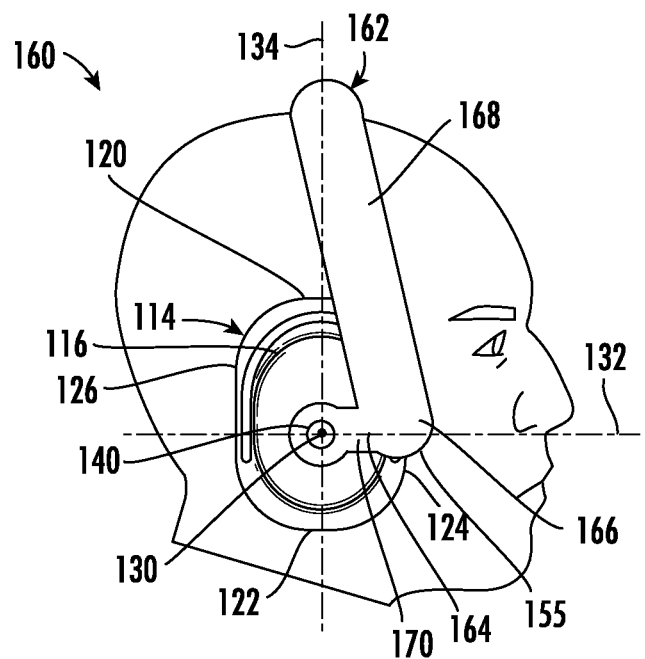
FIG. 4 is an exterior side view of a headband rotated above a user's head with a medial pivot and an offset joint, according to an exemplary embodiment.
Figure 5:
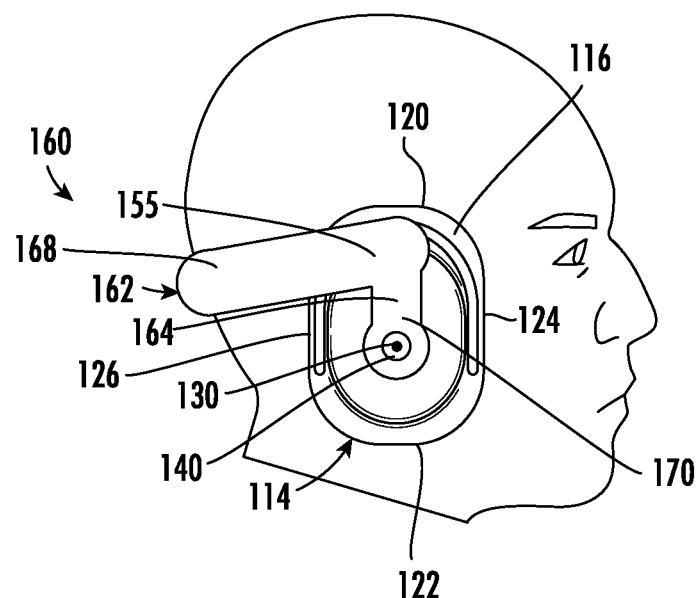
FIG. 5 is an exterior side view of the headband shown in FIG. 4, rotated behind the user's head with a medial pivot and an offset joint, according to an exemplary embodiment.

FIG. 4 and FIG. 5 show earmuffs 160 with headband 162 according to an exemplary embodiment. Headband 162 is "L"-shaped with the lower band segment 164 intersecting (specifically, at an intersection 166) the upper band segment 168 at a substantially perpendicular angle (specifically, between 85 and 95 degrees). In this embodiment, intersection 166 defines a rigid or fixed joint 155, meaning the angle defined between the upper band segment 168 and the lower band segment 164 is not adjustable. In other embodiments, this joint may not be rigid or fixed (for example, may be a pivot joint), meaning the angle defined between the upper band segment 168 and the lower band segment 164 may be user adjustable. The lower band segment 164 is coupled to the exterior of ear cup 114.

Earmuffs 160 are substantially the same as earmuffs 10, 12, and/or 50, except for the differences discussed herein. Additionally, though only one side of the earmuffs 160 are shown here, earmuffs 160 are symmetrical. Thus, for example, the opposite side of earmuffs 160 (not shown) would also include a similar portion of the upper band segment 168 as shown in FIGS. 4 and 5, as well as a second lower band segment that couples to a second ear cup. In this embodiment, a pivot joint 140 is shown at apex 130 of earmuff cup or ear cup 114 (i.e., not off-center). In another embodiment, pivot joint 140 is positioned above horizontal midplane 132. Pivot joint 140 couples the lower band segment 164 to the exterior of ear cup 114. In this embodiment, an offset 170 separates joint 155 from pivot joint 140 along the length of lower band segment 164 and thus creates the off-center joint 155. In this embodiment, the joint 155 is a substantially perpendicular joint (specifically, the angle defined between the upper band segment 168 and the lower segment 164 is between 85 and 95 degrees). In other embodiments the angle formed between the lower band segment 164 and the upper band segment 168 could range between 45 and 135 degrees.

In FIG. 4, headband 162 is shown in a first position in which upper band segment 168 is rotated above a user's head. Here, joint 155 is positioned in front of, on, near, or over front edge 124 and creates a forward bias (e.g., a compressive bias force and/or pressure on front edge 124 that is greater than the compressive force on rear edge 126). Headband 162 defines an "L" shaped headband 162 where joint 155 rotates around pivot joint 140 separated from pivot joint 140 by the offset 170. In FIG. 5, headband 162 is shown in a second position in which upper band segment 168 is rotated behind the user's head. Here, joint 155 is positioned above the horizontal midplane and creates an upward bias (e.g., a compressive bias force and/or pressure on top edge 120 that is greater than the compressive force on bottom edge 122). Between the first position and the second position, headband 162 rotates about pivot joint 140.

Figure 6:
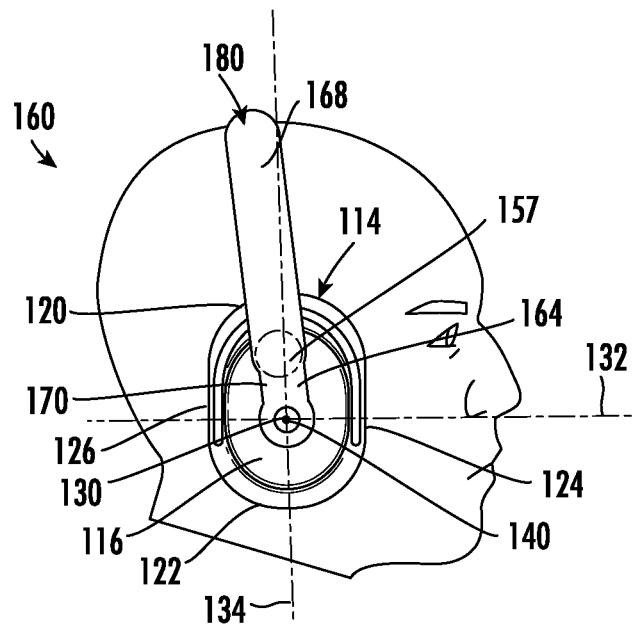
FIG. 6 is an exterior side view of another headband rotated above the user's head with an offset pivot joint located on the headband, according to another exemplary embodiment.
Figure 7:
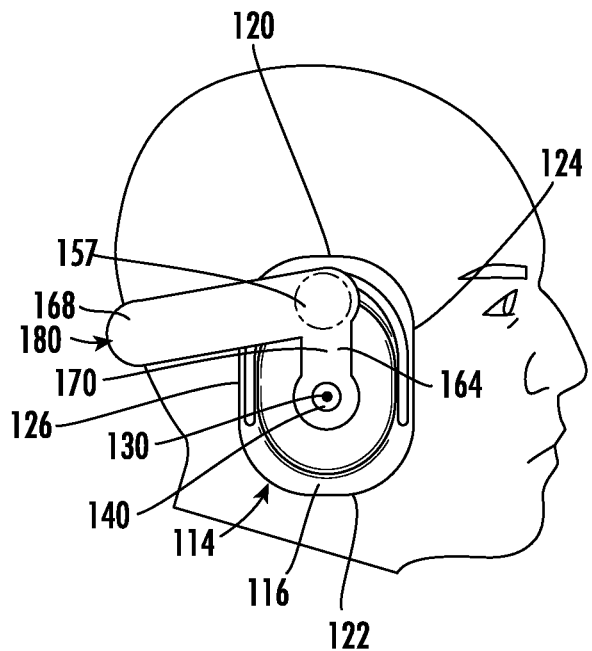
FIG. 7 is an exterior side view of the headband shown in FIG. 6, rotated behind the user's head with an offset pivot joint located on the headband, according to an exemplary embodiment.

FIGS. 6 and 7 show a headband 180, according to an exemplary embodiment. Headband 180 is substantially the same as headband 162 except for the differences discussed herein. FIG. 6 shows headband 180 in a first position in which upper band segment 168 is positioned above the user's head, and FIG. 7 shows headband 180 in a second position in which upper band segment 168 is positioned and locked behind the user's head. Headband 180 has an off-center pivot joint 157. Specifically, upper band segment 168 and lower band segment 164 are pivotably coupled to form pivot joint 157.

In this embodiment, pivot joint 140, which couples headband 180 to ear cup 114, is selectively lockable and may be locked into a fixed position, such that the position of pivot joint 157 remains stationary between horizontal midplane 132 and top edge 120 of cup 114 as the upper band segment 168 is adjusted. For example, when upper band segment 168 rotates from the first position above the user's head (FIG. 6) to the second position behind the user's head (FIG. 7), the location of pivot joint 157, with respect to ear cup 114, does not change and the lower band segment 164 remains substantially upright or vertical. In other embodiments, the headband 180 can be coupled to ear cup 114 by a fixed connection to the outer shell 116, rather than by a pivot joint.

In various embodiments of the headband 180, pivot joint 157 is selectively lockable, such that a user can adjust the force needed to rotate the upper band segment 168 about pivot joint 157 with respect to the lower band segment 164. In some embodiments, headband 180 includes multiple (e.g., other/additional) pivot joints 157. In various embodiments, pivot joint 157 is locked, such that the user can rotate pivot joint 157 about the pivot joint 140 without substantially pivoting upper band segment 168 with respect to lower band segment 164 during rotation. In this embodiment, pivot joint 140 and pivot joint 157 are locking pivots, and the offset 170 is measured between pivot joint 140 and pivot joint 157. The user selectively adjusts pivot joint 157 (or pivot joint 140) to the desired friction to lock or unlock the respective pivot(s). The friction at pivot joint 157 determines how much rotation occurs at pivot joint 157 (e.g., located between horizontal midplane 132 and top edge 120) versus how much rotation occurs at pivot joint 140 (e.g., centrally located at apex 130). This enables the user to selectively change the position of pivot joint 157 and/or adjust pivot joint 157 to enhance and/or customize the compressive bias force/pressure when upper band segment 168 is moved or rotated.

Figure 8A:
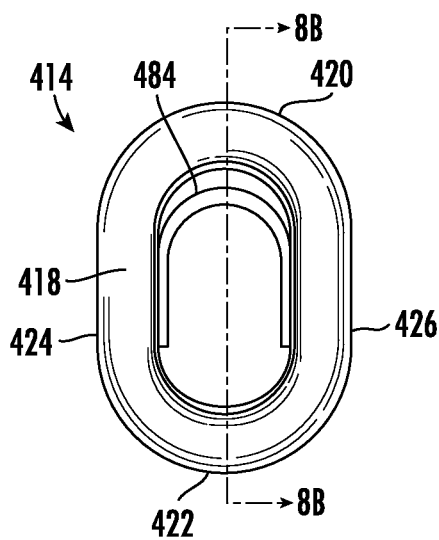
FIG. 8A is an interior side view of an earmuff ear cup, according to an exemplary embodiment.
Figure 8B:
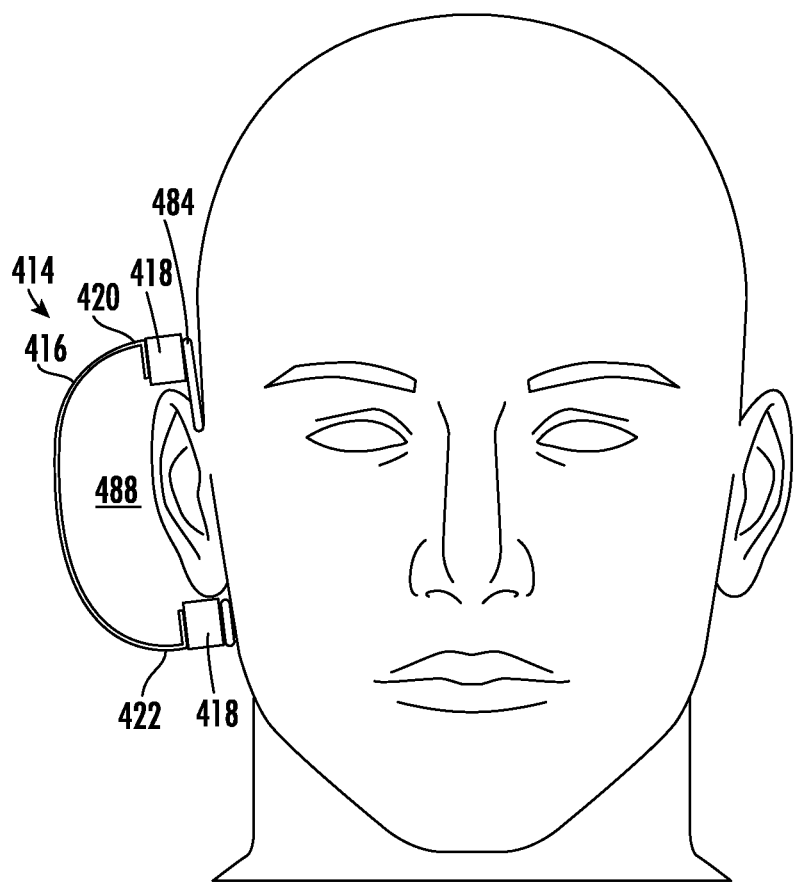
FIG. 8B is a schematic front section view of an earmuff ear cup, according to another exemplary embodiment.
Figure 8C:
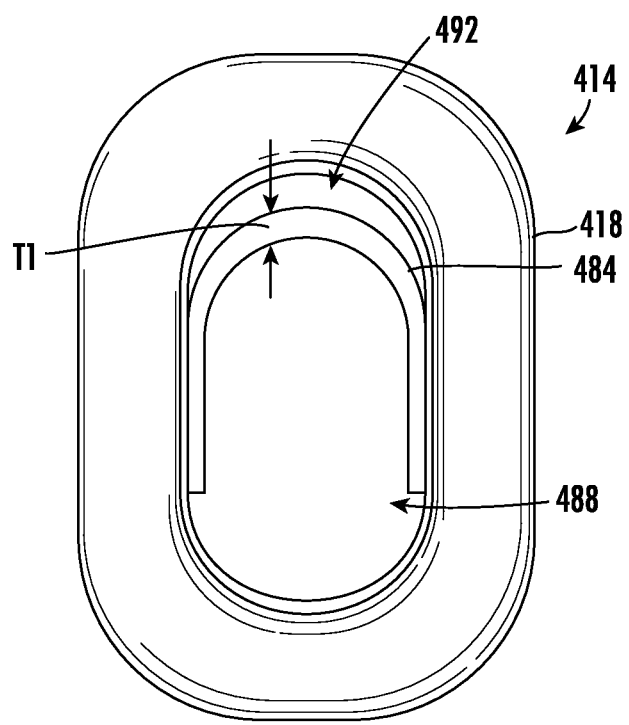
FIG. 8C is an interior side view of an earmuff ear cup, according to another exemplary embodiment.

FIGS. 8A-8C show an earmuff cup or ear cup 414 including an extension or ear loop 484 coupled to or extending from a pad 418. It should be noted that the earmuff cup 414 including ear loop 484 can be utilized as part of any earmuff headband including a headband that generates the biased compressive forces discussed herein. In general, ear loop 484 is an extension that is located below an upper, interior edge of pad 418. In this arrangement, when worn by a user, ear loop 484 rests on the portion of the user's ear that attaches to the head. In this manner, ear loop 484, in combination with pad 418, surrounds the upper portion of the user's ear helping to secure the earmuff cup 414 to the user. This arrangement creates a physical/mechanical constraint that hooks the earmuff on the user's ear to provide better support for the cups 414 which in turn acts to reduce earmuff movement due to forces from walking, going down stairs, jumping, other movements, etc.

As shown best in FIG. 8C, ear loop 484 is a generally D-shaped or U-shaped piece of material (e.g., padded material) that extends between opposing generally vertical portions of pad 418. In this arrangement, ear loop 484 divides the area bounded by pad 418 into lower opening 488 and upper opening 492. When donning earmuffs including cups 414, the user's ear is inserted into lower opening 488 and ear loop 484 is located between the upper portion of the user's ear and the user's head as shown in FIG. 8B. In other words, ear loop 484 creates lower opening 488 to receive the user's ear. Ear loop 484 slides between the ear and the head. As noted, this positioning improves attachment/support to the user's ear and may also act to distribute the compressive bias force over the larger surface area of ear loop 484, which in turn provides a cushion to support the forces that applied to the user's head by the headband.

In various embodiments, ear loop 484 has a thickness T1 that provides for a larger/increased surface area (as compared to an earmuff cup having only pad 418 in contact with the user's head). In some embodiments, the added padding and positioning of ear loop 484 can help mitigate discomfort from a user's ear pressing against glasses.

In some embodiments, the surface area acts to distribute the increased compressive bias forces generated by the various headband designs discussed herein. For example, when headband 411 is rotated behind the user's head, increasing the compressive force along top edge 420 enhances the seal and secures the earmuffs 410 against the head as discussed above, ear loop 484 provides additional surface area that helps distribute that force. In such embodiments, ear loop 484 is coupled to pad 418 and distributes the increased compressive force along both top edge 420 of pad 418 and along the surface area located between the user's ear and head.

Figure 9:
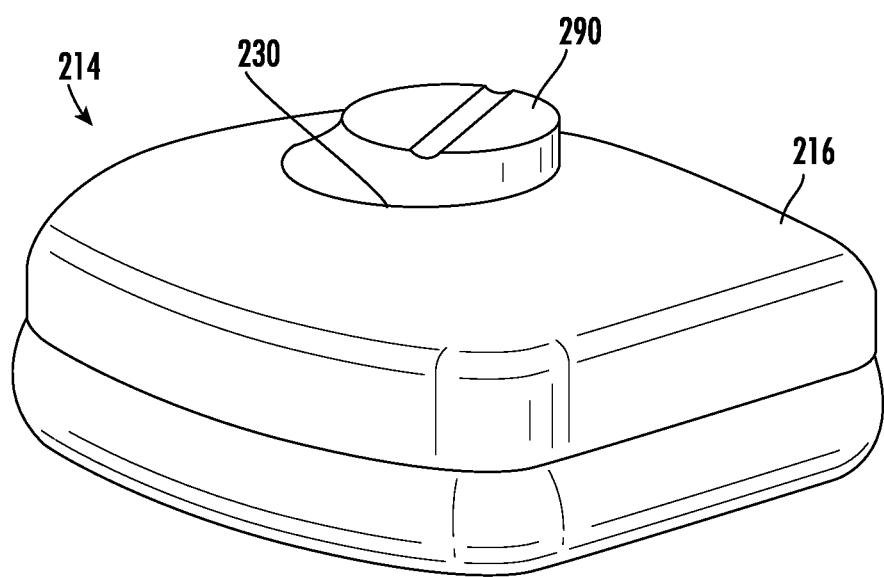
FIG. 9 is a perspective view of an earmuff ear cup having a locking pivot cam that selectively adjusts the compressive bias through rotation of the cam to lengthen/shorten the headband, according to an exemplary embodiment.

FIG. 9 shows another embodiment of an earmuff cup or ear cup 214. Earmuff cup 214 is substantially the same as earmuff cups 14 and 114 except for the differences described herein. Earmuff cup 214 includes a locking pivot cam 290 coupled to the outer shell 216. In this embodiment, cam 290 is positioned at the apex 230 of earmuff cup 214. The locking pivot cam 290 selectively adjusts the compressive bias in a headband, such as headband 11, 13, 52, 162, and/or 180 described above. The user rotates cam 290 to tighten/loosen (e.g., lengthen or shorten) the headband. For example, cam 290 changes hoop stress between the two joints 155 and 140 in headband 162 or the two joints 157 and 140 in headband 180. Thus, rotation of cam 290 increases or decreases hoop stresses in the headband to selectively adjust the compressive bias. In this way, the user can increase the selective bias on top edge of earmuff cup 214 when the headband is rotated behind the head and decrease the compressive bias when headband is rotated above the head.

Figure 10:
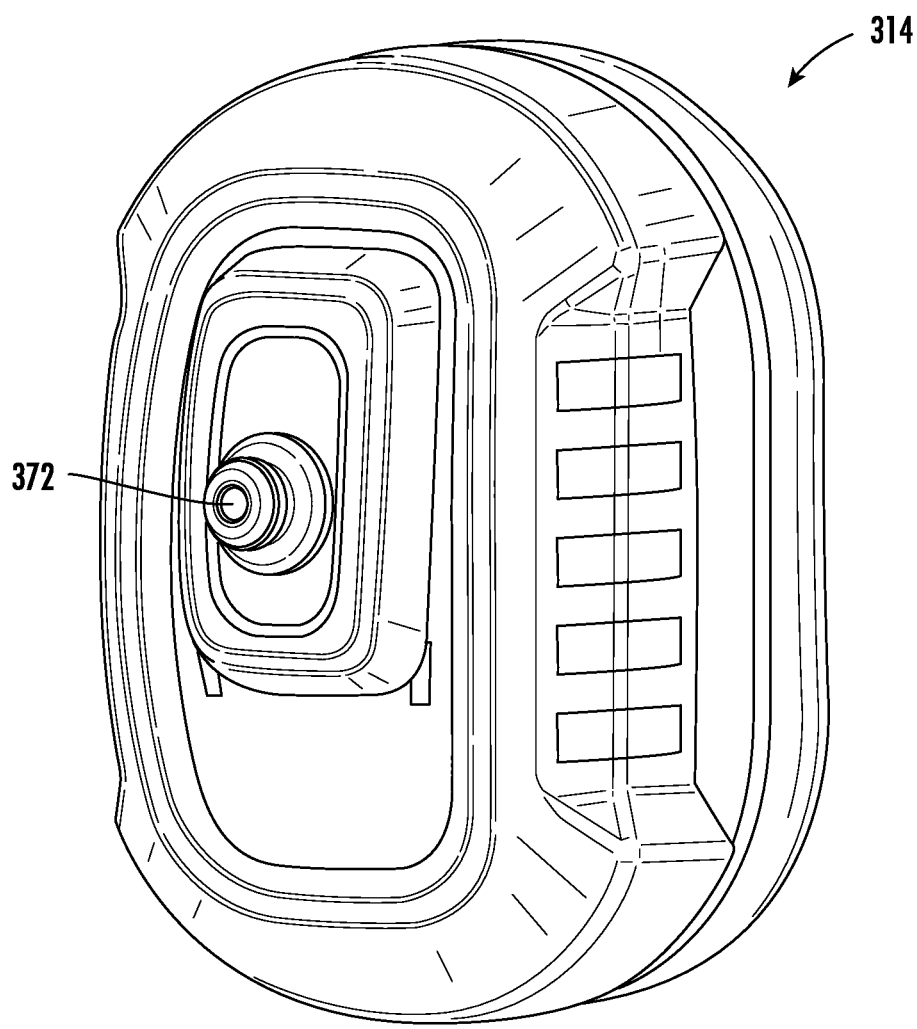
FIG. 10 is a perspective view of an earmuff ear cup having a pivot mount, according to another exemplary embodiment.
Figure 11:
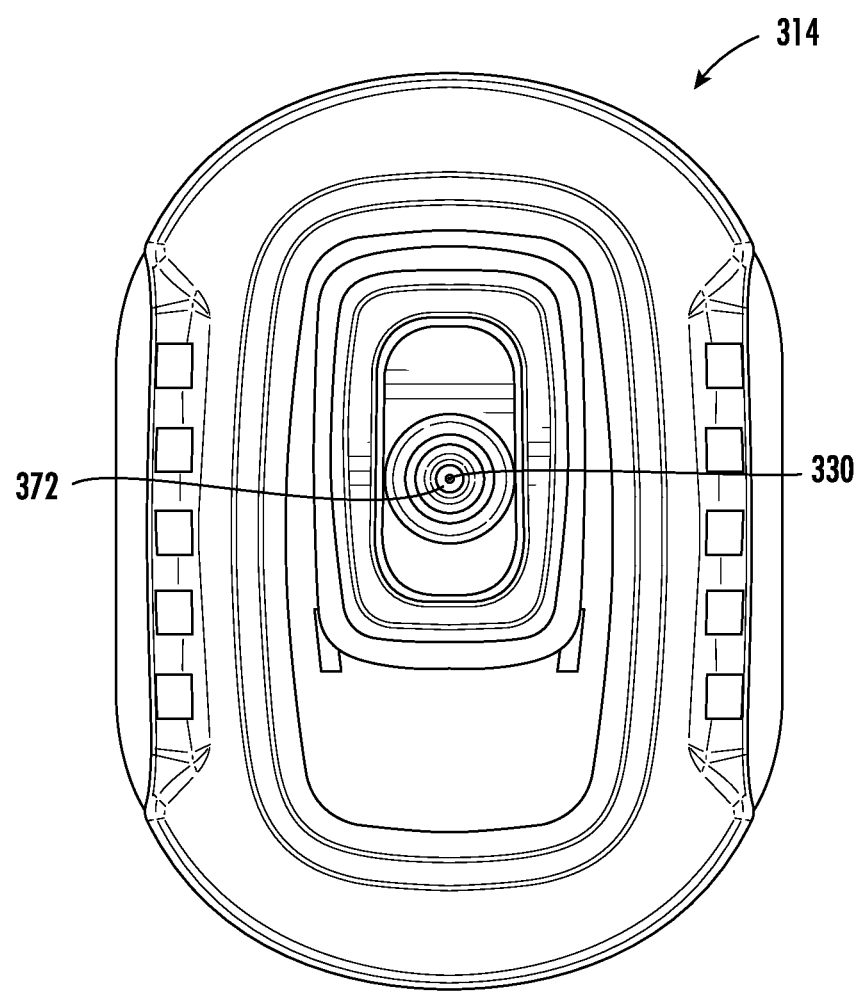
FIG. 11 is an exterior side view of the ear cup shown in FIG. 10.
Figure 12:
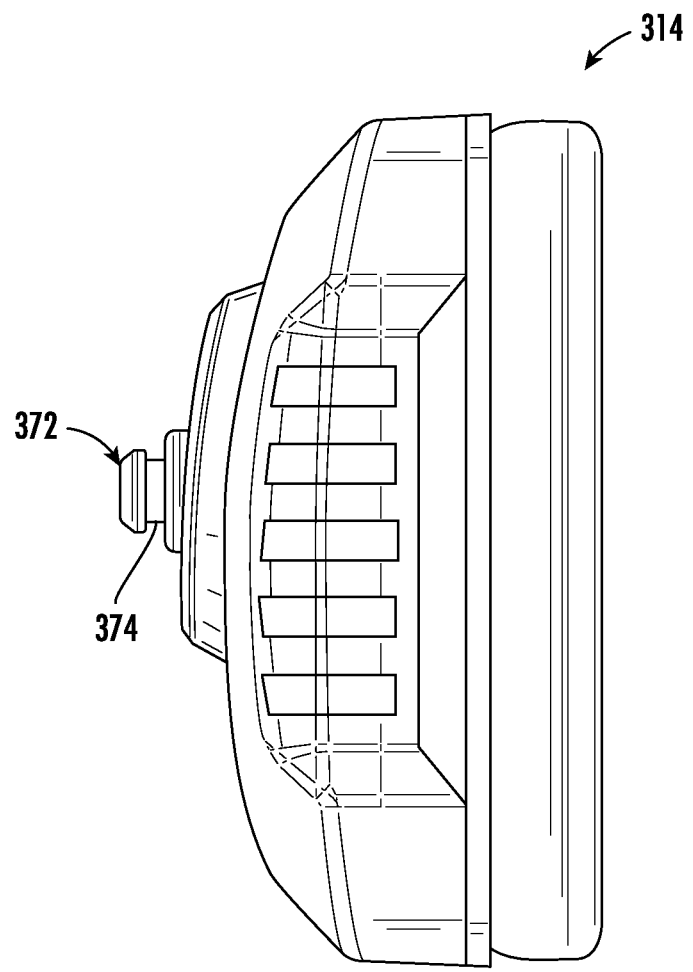
FIG. 12 is a front view of the ear cup shown in FIG. 10.

FIGS. 10-17 shows an earmuff cup or ear cup 314 according to an exemplary embodiment. Earmuff cup 314 is substantially the same as earmuff cup 14 and/or 114 except for the differences discussed herein. Referring to FIGS. 10-12, a pivot mount 372 is coupled to ear cup 314. Pivot mount 372 could be used in connection with any of the embodiments described herein. As shown here, pivot mount 372 is off set from the apex or center 330 of the ear cup 314. In various other embodiments, the pivot mount 372 is positioned at the center 330 of the ear cup 314. Referring to FIG. 12, an exterior annular channel 374 is formed in the exterior surface of pivot mount 372.

Figure 13:
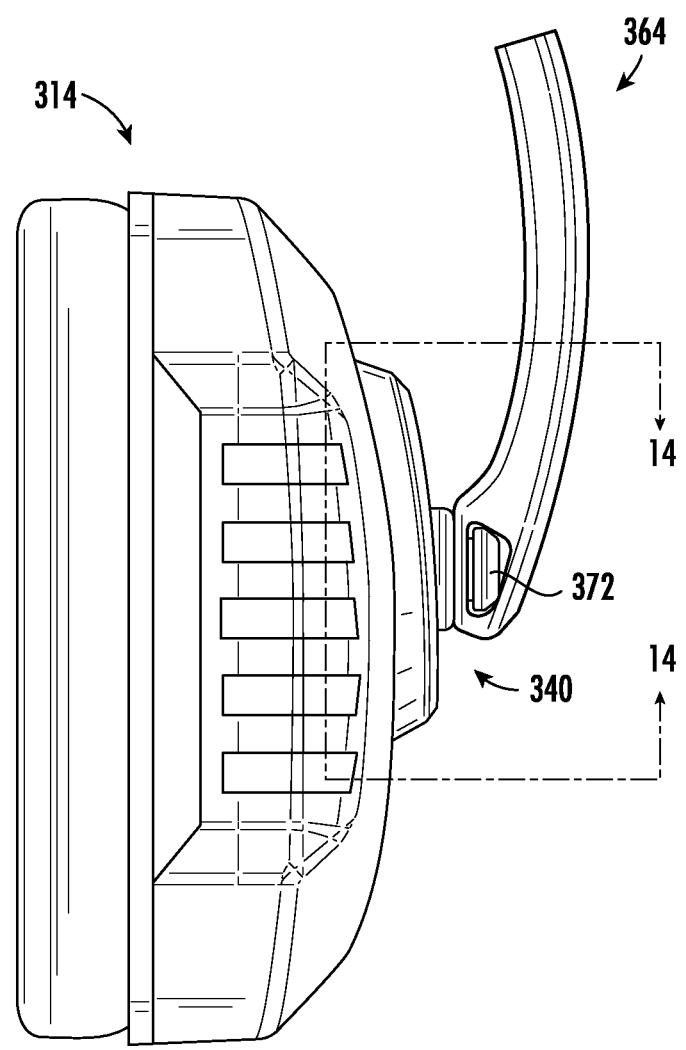
FIG. 13 is a rear view of the ear cup shown in FIG. 10 coupled to the lower segment of an earmuff headband, according to an exemplary embodiment.

Referring to FIG. 13, a lower band segment 364 of a band or headband is connected to the pivot mount 372, to form a pivot joint 340. The pivot joint 340 permits both rotational pivoting of the lower band segment 364 about the pivot mount 372 and forward and rearward pivoting of the lower band segment 364 with respect to the ear cup 314. Specifically, a user can, for example, both rotate the lower band segment 364 from an upright position to a rearward position without significantly moving the ear cup, as well as tilt the ear cup 314 from an angle that supports a seal against a user's ear to an angle that supports generally flush securement to a portion of the user's head behind the ear or to the exterior of a hard had, without significantly bending or flexing the headband to accommodate this shift. The pivot joint 340 permits 360-degree rotation of the lower band segment 364 about the pivot mount 372.

Figure 14:
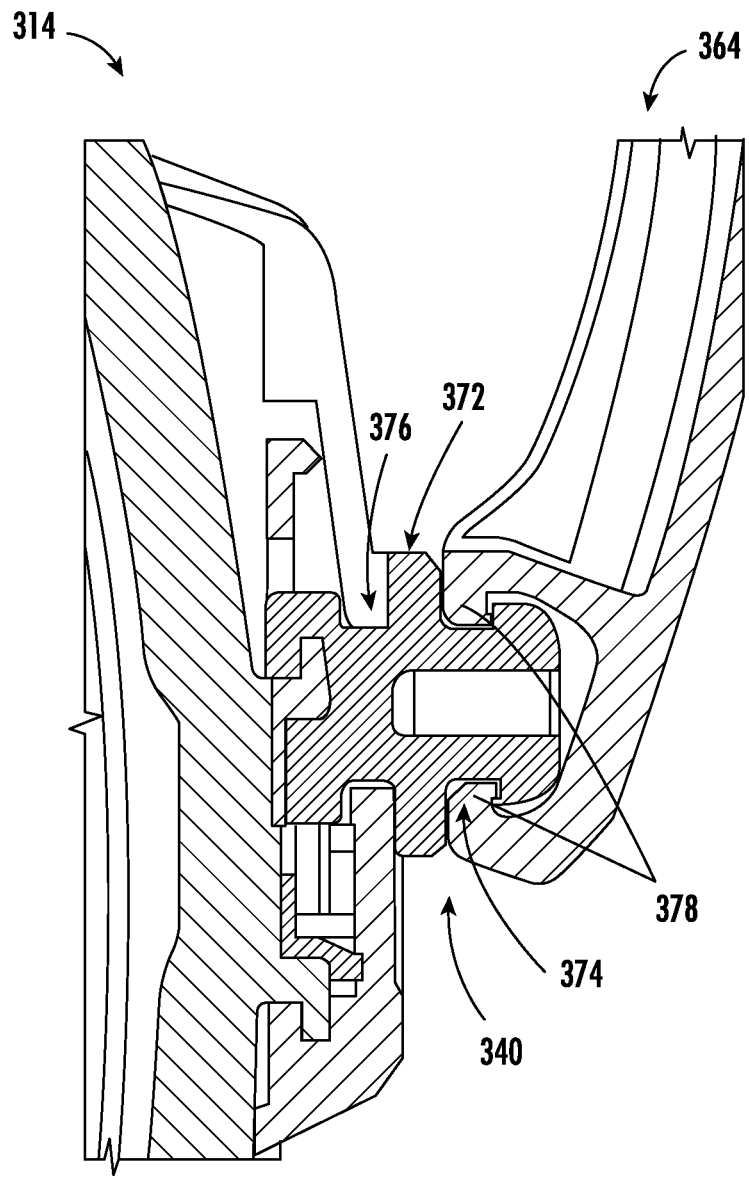
FIG. 14 is a detailed sectional view of the connection between the ear cup and headband segment shown in FIG. 13, taken along line 14-14 in FIG. 13.

Referring to FIG. 14, a detailed cross section is shown of pivot joint 340. Here, the connection between lower band segment 364 and pivot mount 372 can be seen in greater detail. In this embodiment, lower band segment 364 forms an opening. A rib 378 surrounds the opening. The rib 378 mates with the exterior annular channel 374 to tiltably and rotatably couple lower band segment 364 to pivot mount 372, thus forming pivot joint 340. In this embodiment, rib 378 is an annular rib.

Referring to FIG. 15, an exploded view of ear cup 314, along with pivot mount 372, is shown. Additionally, FIG. 16 shows a perspective view of the pivot mount 372. In this embodiment, the pivot mount 372 includes an interior annular channel 376 that is spaced apart from the exterior annular channel 374. Upon assembly, a pair of socket covers 379 are secured around the interior annular channel 376 to couple the pivot mount 372 to the outer shell 316 of ear cup 314. The ear cup 314 also includes an ear pad support 387 that supports an earmuff pad 318.

Figure 17:
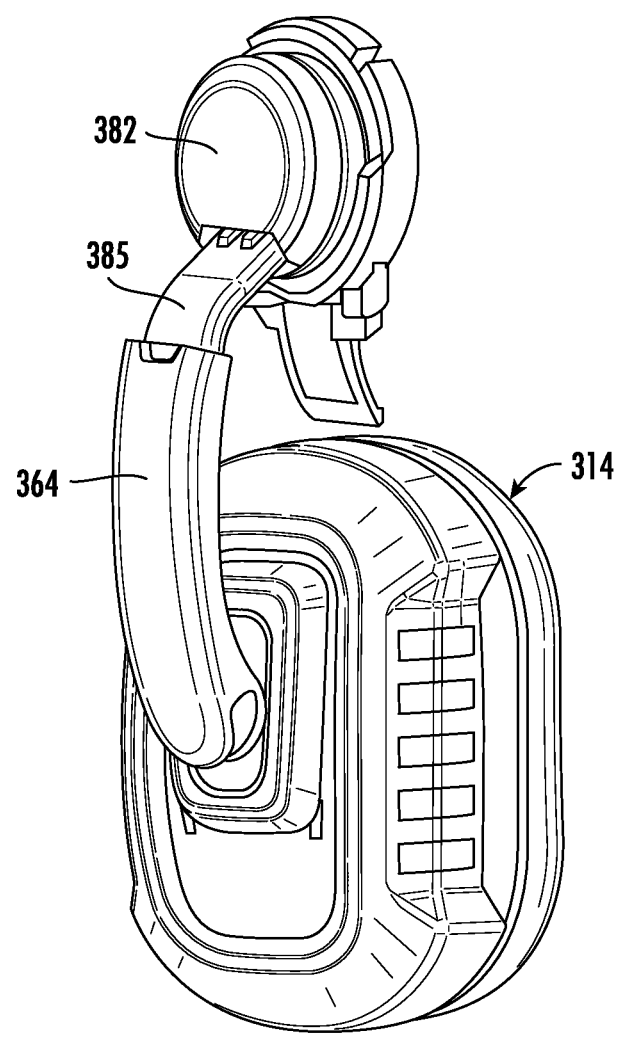
FIG. 17 is an exterior side perspective view of the ear cup and headband shown in FIG. 10 coupled to an upper segment of an earmuff headband and a hard hat clip, according to an exemplary embodiment.
Figure 18:
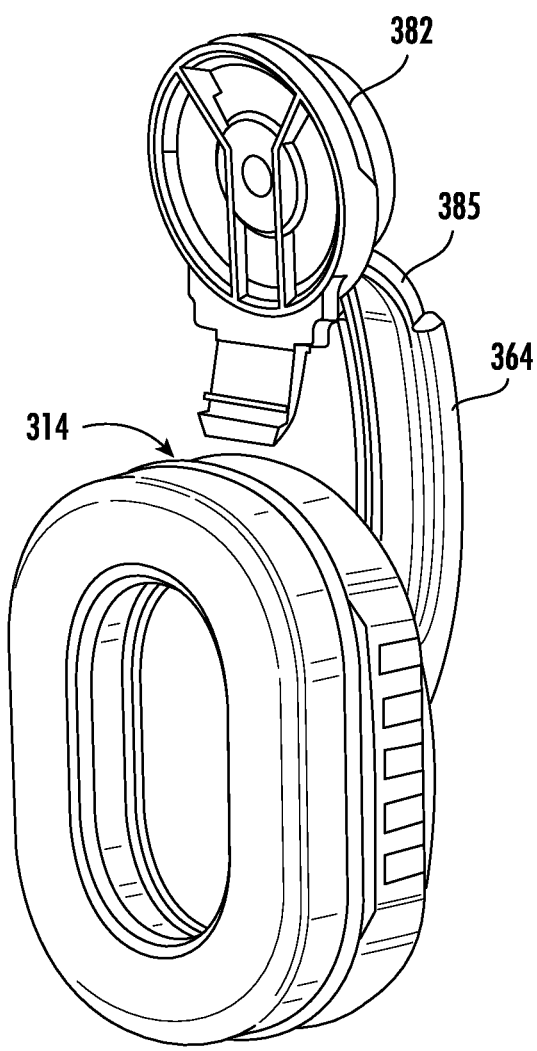
FIG. 18 is an interior side perspective view of the ear cup, upper and lower headband segments, and hard hat clip shown in FIG. 17.

Referring to FIGS. 17-18, a hard hat clip 382 is shown coupled to lower band segment 364 by an upper band segment 385. In various embodiments, an upper portion of an overhead headband could likewise couple to lower band segment 364. During use, hard hat clip 382 rotatably couples to a user's hard hat, such that ear cup 314 can be rotated from a position covering the user's ear to either a position behind the user's ear, or to a position flush against the exterior of the hard hat without substantial repositioning of the hard hat. As discussed above, the tilting and rotational motions permitted by pivot mount 372 permit the ear cup 314 to secured substantially flush against either the space around a user's ear, the space behind the user's ear, or the exterior surface of the hard hat.

It should be understood that the figures illustrate the exemplary embodiments in detail, and it should be understood that the present application is not limited to the details or methodology set forth in the description or illustrated in the figures. It should also be understood that the terminology is for the purpose of description only and should not be regarded as limiting.

Further modifications and alternative embodiments of various aspects of the invention will be apparent to those skilled in the art in view of this description. Accordingly, this description is to be construed as illustrative only. The construction and arrangements shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements. The position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes, and omissions may also be made in the design, operating conditions, and arrangement of the various exemplary embodiments without departing from the scope of the present invention.

For purposes of this disclosure, the term "coupled" means the joining of two components directly or indirectly to one another. Such joining may be stationary in nature or movable in nature. Such joining may be achieved with the two members and any additional intermediate members being integrally formed as a single unitary body with one another or with the two members or the two members and any additional member being attached to one another. Such joining may be permanent in nature or alternatively may be removable or releasable in nature.

In various exemplary embodiments, the relative dimensions, including angles, lengths, and radii, as shown in the Figures, are to scale. Actual measurements of the Figures will disclose relative dimensions, angles, and proportions of the various exemplary embodiments. Various exemplary embodiments extend to various ranges around the absolute and relative dimensions, angles, and proportions that may be determined from the Figures. Various exemplary embodiments include any combination of one or more relative dimensions or angles that may be determined from the Figures. Further, actual dimensions not expressly set out in this description can be determined by using the ratios of dimensions measured in the Figures in combination with the express dimensions set out in this description. In addition, in various embodiments, the present disclosure extends to a variety of ranges (e.g., plus or minus 30%, 20%, or 10%) around any of the absolute or relative dimensions disclosed herein or determinable from the Figures.

What is claimed is:

1. A pair of earmuffs comprising:
   a first ear cup;
   a second ear cup;
   a band comprising,
      a first lower band segment,
      a second lower band segment, and
      an upper band segment extending between the first lower band segment and the second lower band segment;
   a first pivot joint that couples the first lower band segment to the first ear cup; and
   a second pivot joint that couples the second lower band segment to the second ear cup;
   wherein a first angle between 45 degrees and 135 degrees is formed between the upper band segment and the first lower band segment;
   wherein a second angle between 45 degrees and 135 degrees is formed between the upper band segment and the second lower band segment; and
   wherein the band is configured to rotate about the first pivot joint and the second pivot joint from a first position in which the upper band segment is positioned above a user's head to a second position in which the upper band segment is positioned behind a user's head when the first ear cup is positioned over a first ear of the user and the second ear cup is positioned over a second ear of the user.

2. The earmuffs of claim 1, wherein the first lower band segment is rigidly coupled to a first end of the upper band segment such that the first angle is a fixed angle, and wherein the second lower band segment is rigidly coupled to a second end of the upper band segment such that the second angle is a fixed angle.

3. The earmuffs of claim 2, wherein the first angle is between 85 degrees and 95 degrees and wherein the second angle is between 85 degrees and 95 degrees.

4. The earmuffs of claim 1, wherein the first lower band segment is rotatable about the first pivot joint for 360 degrees with respect to the first ear cup and wherein the second lower band segment is rotatable about the second pivot joint for 360 degrees with respect to the second ear cup.

5. The earmuffs of claim 4, wherein the first pivot joint is formed by a first pivot mount that couples the first lower band segment to the first ear cup, the first pivot mount extending from the first ear cup and comprising a first annular channel that mates with a first annular rib formed in the first lower band segment, and wherein the second pivot joint is formed by a second pivot mount that couples the second lower band segment to the second ear cup, the second pivot mount extending from the second ear cup and comprising a second annular channel that mates with a second annular rib formed in the second lower band segment.

6. The earmuffs of claim 1, wherein the first ear cup further comprises a first outer shell and a first ear pad coupled to the first outer shell, the first ear pad configured to surround a user's ear when the earmuffs are worn and the first ear pad comprising an interior perimeter that defines an opening and an ear loop that extends across the opening from a first side of the interior perimeter to a second side of the interior perimeter, and wherein the ear loop is configured to rest on a portion of the first ear of the user that attaches to the user's head.

7. The earmuffs of claim 6, wherein the ear loop is D shaped.

8. The earmuffs of claim 1, wherein the first pivot joint couples the first lower band segment to the first ear cup at a center point of the first ear cup.

9. The earmuffs of claim 1, further comprising a third pivot joint that pivotably couples the upper band segment to the first lower band segment and a fourth pivot joint the pivotably couples the upper band segment to the second lower band segment, wherein the upper band segment pivots about the third and fourth pivot joints relative to the first and second lower band segments to form the first and second angles.

10. A pair of earmuffs comprising:
    a first ear cup;
    a second ear cup; and
    a band comprising,
       a first lower band segment coupled the first ear cup,
       a second lower band segment coupled to the second ear cup,
       an upper band segment coupling the first lower band segment to the second lower band segment,
       a first band pivot joint that couples the upper band segment to the first lower band segment, and
       a second band pivot joint that couples the upper band segment to the second lower band segment;
    wherein the upper band segment is configured to rotate about the first band pivot joint and the second band pivot joint from a first position in which the upper band segment is positioned above a user's head to a second position in which the upper band segment is positioned behind the user's head when the first ear cup is positioned over the first ear of the user and the second ear cup is positioned over a second ear of the user.

11. The earmuffs of claim 10, wherein the first lower band segment is pivotably coupled to the first ear cup and the second lower band segment is pivotably coupled to the second ear cup.

12. The earmuffs of claim 11, further comprising a first selectively adjustable locking pivot mount that couples the first lower band segment to the first ear cup and a second selectively adjustable locking pivot mount that couples the second lower band segment to the second ear cup.

13. The earmuffs of claim 10, further comprising a first pivot mount that couples the first lower band segment to the first ear cup, the first pivot mount extending from the exterior of the first ear cup and comprising an annular channel that mates with a rib formed in the first lower band segment, and a second pivot mount that couples the second lower band segment to the second ear cup, the second pivot mount extending from the exterior of the second ear cup and comprising an annular channel that mates with a rib formed in the second lower band segment.

14. The earmuffs of claim 10, further comprising a cam coupled to the ear cup, the cam configured to lengthen the band when rotated in a first direction and shorten the band when rotated in a second direction opposite the first direction.

15. The earmuffs of claim 10, wherein the first band pivot joint is formed by a first selectively adjustable locking pivot mount and wherein the second band pivot joint is formed by a second selectively adjustable locking pivot mount.

16. An earmuff cup assembly, comprising:
an ear cup, comprising,
an outer shell comprising a first side and a second side opposite the first side, and
an ear pad coupled to the first side of the outer shell;
a pivot mount coupled to the second side of the outer shell, at least a portion of the pivot mount protruding from the outer shell, the pivot mount comprising an exterior annular channel formed in the portion of the pivot mount protruding from the outer shell; and
a first band segment comprising a first end that pivotably mates with the exterior annular channel, a second end opposite the first end, and a surface that forms an opening near the first end, the opening sized to mate the first band segment with the annular channel of the pivot mount;
wherein the first band segment is configured to rotate about the pivot mount and to tilt within the annular channel, such that the second end may be adjusted toward or away from the ear cup.

17. The earmuff cup assembly of claim 16, wherein the first band segment further comprises a rib that surrounds the opening formed in the first end, and wherein the rib mates with the exterior annular channel.

18. The earmuff cup assembly of claim 16, further comprising a second band segment coupled to the first band segment and a clip configured to couple to the exterior of a hard hat coupled to the second band segment.

19. The earmuff cup assembly of claim 16, wherein the pivot mount further comprises an interior annular channel, spaced apart from the exterior annular channel, wherein the interior annular channel mates with one or more portions of the outer shell.

20. The earmuff cup assembly of claim 16, wherein the pivot mount is coupled to the outer shell at the center of the outer shell.

* * * * *